United States Patent [19]

Ohorodnik et al.

[11] 3,957,899

[45] May 18, 1976

[54] PRODUCTION OF MONOVINYLACETYLENE

[75] Inventors: Alexander Ohorodnik, Erftstadt Liblar; Klaus Gehrmann, Erftstadt Lechenich; Günter Legutke, Bruhl;. Hermann Vierling, Hurth, all of Germany

[73] Assignee: Hoechst Aktiengesellschaft, Frankfurt am Main, Germany

[22] Filed: Dec. 10, 1974

[21] Appl. No.: 531,323

[30] Foreign Application Priority Data
Dec. 17, 1973 Germany............................ 2362603

[52] U.S. Cl................................ 260/678; 260/655; C07C/11/22
[51] Int. Cl.²......................................... C07C 21/20
[58] Field of Search..................................... 260/678

[56] References Cited
UNITED STATES PATENTS

| | | | |
|---|---|---|---|
| 1,926,039 | 9/1933 | Downing et al...................... | 260/678 |
| 1,926,055 | 9/1933 | Nieuwland.......................... | 260/678 |
| 2,934,576 | 4/1960 | Goffinet, Jr.......................... | 260/678 |
| 3,142,711 | 7/1964 | Bauchwitz et al................... | 260/678 |
| 3,806,554 | 4/1974 | Ohorodnik et al................... | 260/678 |
| 3,843,743 | 10/1974 | Ohorodnik et al................... | 260/678 |

*Primary Examiner*—Delbert E. Gantz
*Assistant Examiner*—Juanita M. Nelson
*Attorney, Agent, or Firm*—Connolly and Hutz

[57] ABSTRACT

Monovinylacetylene is produced by an improved process, wherein acetylene is introduced at temperatures within the range 40° and 100° C and under acetylene gas pressures within the range 0.01 and 10 atmospheres (gauge) into a Nieuwland catalyst type solution being an aqueous copper(I) chloride solution in hydrochloric acid, which is used in admixture with between 0.1 and 10 weight% of an alkali metal salt of an aminocarboxylic acid or of an aminosulfonic acid, and wherein acetylene is introduced into the catalyst solution jointly and simultaneously with an inert organic solvent extractant and stripping agent for the resulting monovinylacetylene, the solvent being in vapor form and being continuously passed through the catalyst solution so as to continually strip off monovinylacetylene originating from dimerized acetylene.

4 Claims, No Drawings

PRODUCTION OF MONOVINYLACETYLENE

The improved process comprises more particularly concentrating the catalyst solution by evaporating water therefrom and dissolving additional copper (I) chloride in the catalyst solution so concentrated.

U.S. Pat. No. 3,806,554 inter alia describes a process for making monovinylacetylene, wherein acetylene is introduced at temperatures within the range 40° and 100°C and under acetylene gas pressures within the range 0.01 and 10 atmospheres gauge into a Nieuwland catalyst type solution being an aqueous copper(I) chloride solution in hydrochloric acid, which is used in admixture with between 0.1 and 10 weight% of an alkali metal salt of an aminocarboxylic acid or of an aminosulfonic acid, which process comprises introducing, into the catalyst solution, acetylene jointly and simultaneously with an inert organic solvent extractant and stripping agent for the resulting monovinylacetylene, the solvent being used in vapor form and being continuously passed through the catalyst solution so as to continually strip off monovinylacetylene originating from dimerized acetylene.

We have now unexpectedly found that it is possible to even further and considerably improve the acetylene conversion rates, for substantially unchanged monovinylacetylene yields, based on the acetylene transformed, by modifying or improving the process described in U.S. Pat. No. 3,806,554, the modification or improvement comprising concentrating the catalyst solution by evaporating water therefrom and dissolving additional copper(I) chloride in the catalyst solution so concentrated.

Further preferred features of the present process provide:

a. for additional copper (I) chloride to be dissolved in the concentrated catalyst solution until it is saturated therewith;

b. for the catalyst solution to be concentrated in the reaction zone by evaporating the water therefrom by the introduction of acetylene:

c. for a density within the range 1.85 and 2.5 kg/l, preferably within the range 1.9 and 2.1 kg/l, to be established in the catalyst solution; and d. for a molar ratio of copper(I) chloride to alkali metal chloride or ammonium chloride complex former within the range 1.1 : 1.0 and 1.5 : 1.0, preferably within the range about 1.3 : 1.0, to be established in the catalyst solution.

The alkali metal salt of aminocarboxylic acid or aminosulfonic acid should preferably be selected from those of nitrilotriacetic acid, ethylenediaminotetracetic acid, ortho-, meta- or paraaminobenzoic acid, taurine, glycine, $\alpha$- or $\beta$-alanine.

Further preferred features of the present process, which are the same as those used in the processes described in German published Specification "Offenlegungsschrift" 1,543,129 and in the above U.S.Patent, comprise:

a. introducing the inert solvent in liquid or vapor form into the catalyst solution;

b. using an inert solvent boiling at temperatures between about 20°C and less than 100°C;

c. using the inert solvent in proportions substantially within the range 5 and 50 % by volume, based on the total gas volume; and d. selecting the inert solvent from methanol, benzene, chloroform, acetonitrile, acetone, n-hexane or methylethylketone.

Nieuwland catalyst solutions having a density within the range 1.3 and 1.8 kg/l, preferably within the range 1.5 and 1.6 kg/l, more preferably 1.58 kg/l, are normally used in the art for making monovinylacetylene. Lower densities effect the decomposition of the catalytically active copper complex, whereas higher densities impair both the conversion rate and monovinylacetylene yield, based on the acetylene transformed. This is the reason why catalyst solutions which have a density of 1.58 kg/l and are approximately composed of 34.5 weight% of CuCl, 24.5 weight% of KCl, 0.1 weight% of HCl and 40.9 weight% of $H_2O$, are preferred in industry.

A catalyst having the composition just indicated contains CuCl and KCl in a molar ratio of 1.05 : 1.00 (cf. comparative Example 1 hereinafter).

Such prior art catalyst can be activated in accordance with the present invention by the following steps:

I. Preparation of a catalyst solution of high density

The simplest way of achieving this comprises concentrating the above Nieuwland catalyst solution containing CuCl and KCl in a molar ratio of 1.05 : 1.00, preferably in the reactor itself. To this end, it is advantageous for the water expelled from the catalyst solution under the reaction conditions by means of acetylene, which is passed therethrough, to be left unsubstituted until the solution has the desirable density, Needless to say, the density and composition of the catalyst solution are changed thereby. For example, a catalyst solution having a density of 1.90 kg/l is composed of 37.5 weight% of CuCl, 27.5 weight% of KCl, 0.2 weight% of HCl and 34.8 weight% of $H_2O$.

The initial 1.05 : 1.00 molar ratio of CuCl : KCl remains unaffected.

A catalyst solution merely concentrated is, however, not very suitable for use in making monovinylacetylene under standard conditions, as it impairs the acetylene conversion rates and monovinylacetylene yields, based on the acetylene transformed.

II. Increasing the CuCl : KCl-ratio in the catalyst solution.

As has unexpectedly been found, it is possible for considerable additional quantities of CuCl to be dissolved in a concentrated catalyst solution, i.e. in a solution containing less water than initially. The Nieuwland catalyst with a density of 1.58 kg/l, which is normally used in industry, is saturated with CuCl, for a molar ratio of CuCl : KCl equal to 1.05 : 1.00. On the other hand, however, about a further 170 g CuCl/l is absorbed at 80°C by a concentrated catalyst solution having a density of 1.90 kg/l. The unexpected result that additional copper(I) chloride can be dissolved in a concentrated catalyst solution without any need to add more complex former thereto, makes it possible for the CuCl : KCl-ratio in the catalyst solution to be increased. In the present case, the CuCl - KCl-ratio is increased from initially 1.05 : 1.00 to 1.30 : 1.00. A catalyst so concentrated and charged with additional CuCl has a particularly good activity which ensures high acetylene conversion rates. Even if so modified, it is necessary for the catalyst solution, which enables high acetylene conversion rates to be obtained at the price of reduced monovinylacetylene yields, to be further treated so as to be suitable for use in the commercial production of monovinylacetylene.

To ensure optimum working conditions, it is necessary for the treatment steps of the present invention to be combined with the process described in U.S. Pat. No. 3,806,554. If this is done, it is possible for the acetylene conversion rate to be increased considerably from 17 – 18 % to more than 25 %, for substantially unchanged monovinylacetylene yields of more than 94 %, based on the acetylene transformed.

The statements made in U.S. Pat. No. 3,806,554 are incidentally also true concerning the present invention.

The following comparative Examples 1 and 2 illustrate the behaviour of a prior art Nieuwland catalyst. Comparative Example 2 illustrates more particularly the improved yield obtainable with the catalyst of Example 1 provided that resulting monovinylacetylene is expelled from the reaction zone by stripping with acetone.

Comparative Example 3 illustrates the behaviour of the catalyst used in Example 1 and improved by the addition of 2.6 weight% of sodium salt of nitrilotriacetic acid (cf. U.S. Pat. No. 3,806,554).

Comparative Example 4 describes the combined use of the steps disclosed in Examples 2 and 3, respectively, i.e. a further feature of U.S. Pat. No. 3,806,554, and Example 5 illustrates the present invention.

EXAMPLE 1: (Comparative Example)

A jacketed reactor 1.5 m high with an internal diameter of 5 cm was fed with 5 l of a Nieuwland catalyst solution composed of 34.5 weight% of copper(I) chloride,
24.5 weight% of potassium chloride,
0.1 weight% of hydrogen chloride and
40.9 weight% of water.

The solution had a density of 1.58 kg/l at 80°C.

The catalyst solution was heated to 80°C and a gas mixture of 560 normal liters/hr (S.T.P.) of acetylene and 190 normal liters/hr of nitrogen was introduced thereinto, through the bottom portion of the reactor. The following reaction conditions were maintained constant:

| | |
|---|---|
| Reaction temperature: | 80°C |
| Gas pressure at reactor inlet: | 0.2 atm. gauge |
| Gas load: | 150 l gas/l catalyst |
| Composition of gas: | 75 % by vol. acetylene |
| | 25 % by vol. nitrogen |

The gas coming from the reactor was subjected to gaschromatography and the results obtained were used to identify the acetylene conversion rate and monovinylacetylene yield. Three evaluations were made so as to obtain a mean value which is indicated in the Table hereinafter.

EXAMPLE 2: (Comparative Example)

The procedure was the same as that described in Example 1 save that the nitrogen in the gas mixture was replaced by the same quantity (25 % by volume) of acetone in vapor form. The reaction gas was analyzed and the test results were evaluated in the manner described in Example 1. The results obtained are indicated in the Table hereinafter.

EXAMPLE 3: (Comparative Example)

The procedure was the same as that described in Example 1 save that 2.6 weight% of sodium salt of nitrilotriacetic acid was added to the catalyst solution.

EXAMPLE 4: (Comparative Example)

The procedure was the same as that described in Example 1 save that 2.6 weight% of sodium salt of nitrilotriacetic acid was added to the catalyst solution and that the nitrogen in the gas mixture was replaced by the same quantity (25 % by volume) of acetone in vapor form.

The reaction gas was analyzed and the test results were evaluated in the manner described in the preceding Examples.

EXAMPLE 5:

A catalyst solution having the composition indicated in Example 1 was gradually concentrated. To this end, the water expelled therefrom by the introduction of acetone as left unsubstituted. As soon as the catalyst solution had a density of 1.90 kg/l, CuCl was added portionwise thereto. Altogether 170 g of additional CuCl/l catalyst could be dissolved therein, whereby the CuCl : KCl-ratio was increased from initially 1.05 : 1.00 to 1.30 : 1.00 and the density was increased from 1.90 kg/l to 2.06 kg/l. The catalyst solution so activated was admixed with 2.6 weight% of sodium salt of nitrilotriacetic acid and acetylene and acetone in vapor form were passed through the catalyst solution, as in Example 4.

The composition and density of the various catalysts are indicated in Table 1 and the results obtained therewith are indicated in Table 2.

Table 1

| Ex. | Catalyst composition, wgt.% | | | | Ratio CuCl:KCl | Density Kg/l | Catalyst addition | Catalyst addition |
|---|---|---|---|---|---|---|---|---|
| | CuCl | KCl | HCl | $H_2O$ | | | | |
| 1 | 34.5 | 24.5 | 0.1 | 40.9 | 1.05 : 1.00 | 1.58 | — | — |
| 2 | 34.5 | 24.5 | 0.1 | 40.9 | 1.05 : 1.00 | 1.58 | — | 25 Vol%$N_2$ replaced by acetone |
| 3 | 34.5 | 24.5 | 0.1 | 40.9 | 1.05 : 1.00 | 1.58 | 2.6 wgt.% NTE-salt | — |
| 4 | 34.5 | 24.5 | 0.1 | 40.9 | 1.05 : 1.00 | 1.58 | 2.6 wgt.% NTE-salt | 25 Vol%$N_2$ replaced by acetone |
| 5 | 42.7 | 25.1 | 0.2 | 32.0 | 1.30 : 1.00 | 2.06 | 2.6 wgt.% NTE-salt | 25 Vol%$N_2$ replaced by acetone |

NTE-salt = Sodium salt of nitrilotriacetic acid

Table 2

| Example | 1 | 2 | 3 | 4 | 5 |
|---|---|---|---|---|---|
| Acetylene conversion rate (%) | 17.6 | 16.8 | 18.4 | 17.7 | 25.5 |

Table 2-continued

| Example | 1 | 2 | 3 | 4 | 5 |
|---|---|---|---|---|---|
| Mova-yield, based on acetylene transformed, in % | 77.7 | 89.1 | 90.5 | 95.0 | 94.1 |
| Diva | 15.3 | 8.0 | 6.7 | 2.3 | 2.5 |
| Acetaldehyde | 5.8 | 2.5 | 2.4 | 2.3 | 2.4 |
| VC, CB and MVK | balance | balance | balance | balance | balance |
| Mova-concentraion in reaction gas (% by volume) | 5.1 | 7.4 | 7.9 | 8.3 | 11.8 |

Mova = Monovinylacetylene
CB = 2-Chlorbutadiene-(1,3)
Diva = Divinylacetylene
MVK = Methylvinylketone
VC = Vinylchloride

We claim:

1. In a process for making monovinylacetylene, wherein acetylene is introduced at temperatures within the range 40° and 100°C and under acetylene gas pressures within the range 0.01 and 10 atmospheres (gauge) into a Nieuwland and catalyst type solution being an aqueous copper(I) chloride solution in hydrochloric acid, which is used in admixture with between 0.01 and 10 weight% of an alkali metal salt of an aminocarboxylic acid or of an aminosulfonic 0.1 and wherein acetylene is introduced into the catalyst solution jointly and simultaneously with an inert organic solvent extractant and stripping agent for the resulting monovinylacetylene, the solvent being in vapor form and being continuously passed through the catalyst solution so as to continually strip off monovinylacetylene originating from dimerized acetylene, the improvement which comprises concentrating the catalyst solution by evaporating water therefrom and dissolving additional copper(I) chloride in the catalyst solution so concentrated thereby establishing a molar ratio of copper (I) chloride to alkali metal chloride or ammonium chloride complex former within the range 1.1:1.0 and 1.5:1.0 in the catalyst solution.

2. A process as claimed in claim 1, wherein additional copper (I) chloride is dissolved in the concentrated catalyst solution until it is saturated therewith.

3. A process as claimed in claim 1, wherein the catalyst solution is concentrated in the reaction zone itself by evaporating water therefrom by the introduction of acetylene.

4. A process as claimed in claim 1, wherein a density within the range 1.85 and 2.5 kg/l is established in the catalyst solution.

* * * * *

UNITED STATES PATENT AND TRADEMARK OFFICE
CERTIFICATE OF CORRECTION

PATENT NO. : 3,957,899
DATED : May 18, 1976
INVENTOR(S) : Ohorodnik et al

It is certified that error appears in the above-identified patent and that said Letters Patent are hereby corrected as shown below:

Column 5 claim 1 line 8 change "0.01" to --0.1--.

Column 5 claim 1 line 9 change "0.1" to --acid,--.

Signed and Sealed this

Twenty-eighth Day of December 1976

[SEAL]

*Attest:*

RUTH C. MASON
*Attesting Officer*

C. MARSHALL DANN
*Commissioner of Patents and Trademarks*